United States Patent
Kamal et al.

(10) Patent No.: US 9,085,557 B2
(45) Date of Patent: Jul. 21, 2015

(54) QUINOLYLPIPERAZINO SUBSTITUTED THIOLACTONE COMPOUNDS AND PROCESS FOR THE PREPARATION THEREOF

(75) Inventors: Ahmed Kamal, Hyderabad (IN); Azeeza Shaik, Hyderabad (IN); Ahmad Ali Shaik, Hyderabad (IN); Mohammed Shaheer Malik, Hyderabad (IN); Inshad Ali Khan, Jammu (IN); Sheikh Tasduq Abdullah, Jammu (IN); Sandeep Sharma, Jammu (IN); Anshu Beulah Ram, Jammu (IN)

(73) Assignee: Council of Scientific and Industrial Research, New Delhi (IN)

( * ) Notice: Subject to any disclaimer, the term of this patent is extended or adjusted under 35 U.S.C. 154(b) by 210 days.

(21) Appl. No.: 13/643,133

(22) PCT Filed: May 6, 2011

(86) PCT No.: PCT/IB2011/000962
§ 371 (c)(1),
(2), (4) Date: Apr. 10, 2013

(87) PCT Pub. No.: WO2011/138666
PCT Pub. Date: Nov. 10, 2011

(65) Prior Publication Data
US 2013/0190489 A1    Jul. 25, 2013

(30) Foreign Application Priority Data
May 6, 2010   (IN) .................... 1069/DEL/2010

(51) Int. Cl.
| | | |
|---|---|---|
| *A61K 31/551* | (2006.01) | |
| *A61K 31/4725* | (2006.01) | |
| *C07D 409/14* | (2006.01) | |
| *C07D 409/12* | (2006.01) | |

(52) U.S. Cl.
CPC ............ *C07D 409/12* (2013.01); *C07D 409/14* (2013.01)

(58) Field of Classification Search
CPC ............... C07D 409/14; A61K 31/551; A61K 31/314725
USPC ............... 514/218, 253.06; 540/597; 544/363
See application file for complete search history.

(56) References Cited

FOREIGN PATENT DOCUMENTS
| | | |
|---|---|---|
| WO | 2005/070430 A1 | 8/2005 |
| WO | 2006/038172 A1 | 4/2006 |

OTHER PUBLICATIONS

Kamal et al, Antitubercular agents. Part 2: New thiolactomycin analogues active against *Mycobacterium tuberculosis*, Bioorganic & Medicinal Chemistry Letters, Pergamon, Elsevier Science, GB, vol. 15, No. 7, Apr. 1 2005, pp. 1927-1929, XP025313495, ISSN: 0960-894X, DOI:DOI10.1016/J.BMCL.2005.01.84 (retrieved on Apr. 1, 2005).

International Search Report, European Patent Office in its capacity as the International Searching Authority on Jul. 15, 2011 in the counterpart International Application No. PCT/IB2011/00962.

*Primary Examiner* — Brenda Coleman
(74) *Attorney, Agent, or Firm* — Gottlieb, Rackman & Reisman, P.C.

(57) ABSTRACT

The present invention provides compounds of general formula A, useful as potential anti-tubercular agents against *Mycobacterium tuberculosis* H37Rv, and drug-resistant *Mycobacterium tuberculosis* and a process for the preparation thereof Formula A

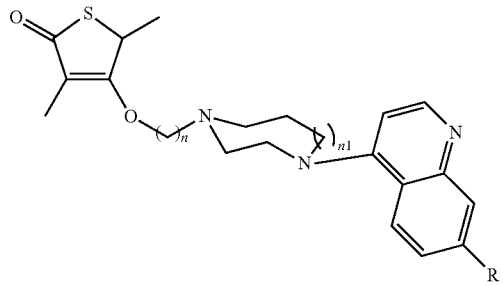

wherein,
n=5-12
$n_1$=0,1
R=$CF_3$ or Cl.

13 Claims, 2 Drawing Sheets

Figure 1:
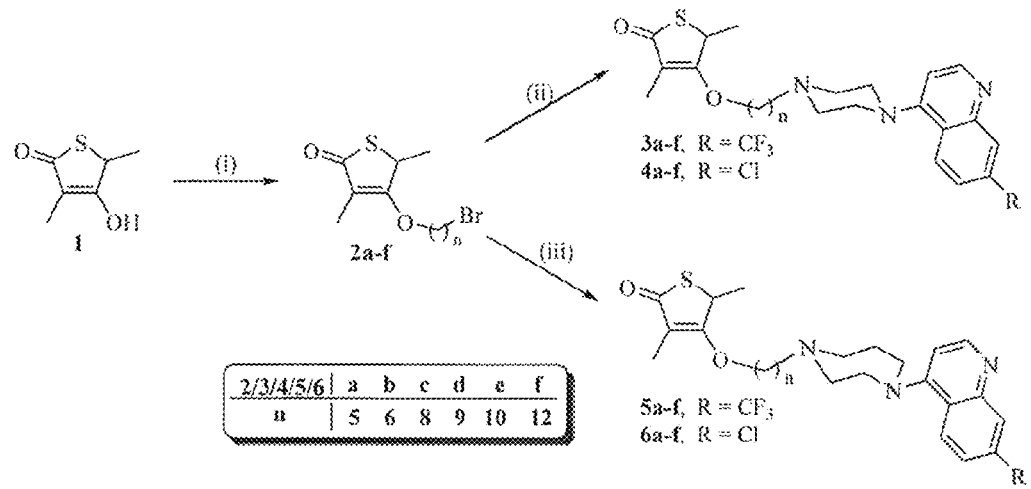
Figure 1:
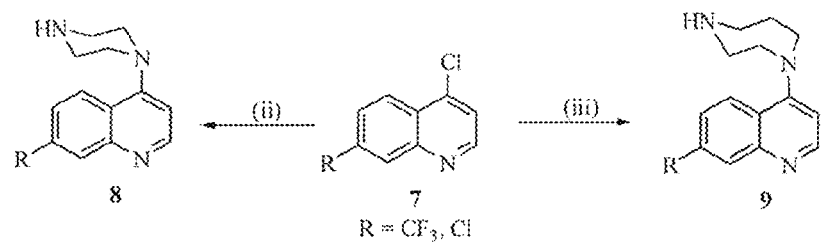
Figure 2:
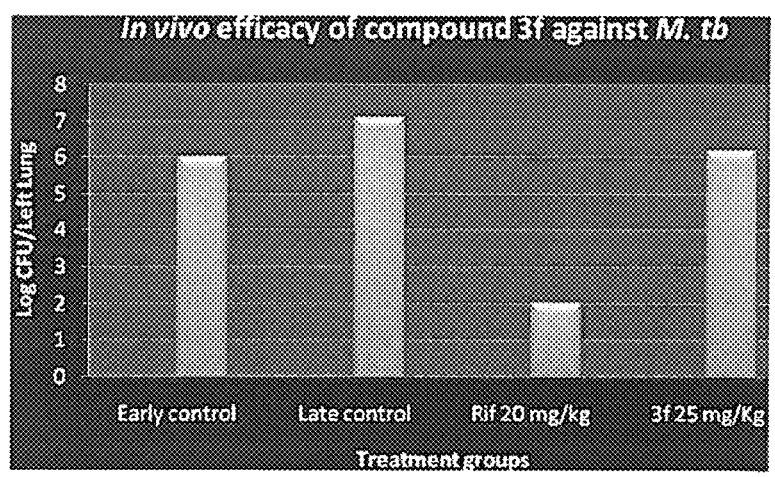

QUINOLYLPIPERAZINO SUBSTITUTED THIOLACTONE COMPOUNDS AND PROCESS FOR THE PREPARATION THEREOF

This application is a national stage application filed under 35 U.S.C. 371 of PCT/IB11/00962, filed May 6, 2011.

FIELD OF THE INVENTION

The present invention relates to quinolylpiperazino substituted thiolactone compounds as anti-tubercular antibiotics and process for the preparation thereof. More particularly, the present invention relates to the synthesis of a new class of quinolylpiperazino compounds of thiolactomycin as useful anti-tubercular agents.

BACKGROUND OF THE INVENTION

Over the past few years, our research efforts have been focused on the exploration of novel scaffolds with antimycobacterial activity and eventually to develop new anti-tubercular agents that can improve the current therapeutic regimen as well as effective in the treatment of MDR-TB (Kamal, A.; Babu, A. H.; Ramana, A. V.; Sinha, R.; Yadav, J. S.; Arora, S. K. *Bioorg. Med. Chem. Lett.* 2005, 15, 1923-1926.; Kamal, A.; Reddy, K. S.; Ahmed, S. K.; Khan, M. N. A.; Sinha, R. K.; Yadav, J. S.; Arora, S. K. *Bioorg. Med. Chem.* 2006, 14, 650-658.; Kamal, A.; Ahmed, S. K.; Reddy, K. S.; Khan, M. N. A.; Shetti, R. V. C. R. N. C.; Siddhardha, B.; Murthy, U. S. N.; Khan, I. A.; Kumar, M.; Sharma, S.; Ram, A. B. *Bioorg. Med. Chem. Lett.* 2007, 17, 5419-5422; Kamal, A.; Azeeza, S.; Malik, M. S.; Faazil, S. *Int. J. of Medical and Biological Frontiers* 2010, 16, 535-568).

Thiolactomycin (TLM) is a thiolactone antibiotic isolated from a soil sample collected in Sayama city, Saitama prefecture, Japan. It is obtained from fermentation broth of *Nocardia* species, a strain of *Actinomycetes* (Oishi, H.; Noto, T.; Sasaki, H.; Suzuki, K.; Hayashi, T.; Okazaki, H.; Ando, K.; Sawada, M. *J Antibiot.* (Tokyo) 1982, 35, 391-395.; Sasaki, H.; Oishi, H.; Hayashi, T.; Noto, T.; Ando, K.; Sawada, M. *J. Antibiot.* (Tokyo) 1982, 35, 396-400.; Nishida, I.; Kawaguchi, A.; Yamada, M. *J. Biol. Chem.* 1986, 99, 1447-1454).

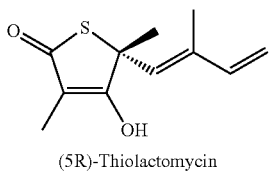

(5R)-Thiolactomycin

TLM exhibits potent in vitro and in vivo activity against many pathogenic bacteria, including Gram-negative and Gram-positive bacteria and *M. tuberculosis*. It inhibits bacterial and plant type II fatty acid synthases (FAS-II) but not mammalian or yeast type I fatty acid synthases (FAS-I). In *Escherichia coli* TLM inhibits both β-ketoacyl-ACP synthase I to III and acetyl coenzyme A (CoA): ACP transacylase activities at in vitro and in vivo conditions. However, the above activity is interesting but it is insufficient to warrant further progression of thiolactomycin itself as an anti-TB agent. Therefore, new analogues of thiolactomycin needs to be designed and synthesized that could exhibit potential activity against *M. tuberculosis* cultures. (Slayden, R. A.; Lee, R. E.; Armour, J. W.; Cooper, A. M.; Orme, I. M.; Brennan, P. J.; Besra, G. S. *Antimicrob. Agents Chemother.* 1996, 40, 2813-2819.; Noto, T.; Miyakawa, S.; Oishi, H.; Endo, H.; Okazaki, H. *J. Antibiot.* (Tokyo) 1982, 35, 401-410.; Hayashi, T.; Yamamoto, O.; Sasaki, H.; Kawaguchi, A.; Okazaki, H. *Biochem. Biophys. Res. Commun.* 1983, 115, 1108-1113.; Tsay, J. T.; Rock, C. O.; Jackowski, S. *J. Bacteriology* 1992, 174, 508-513).

In this laboratory a number of C-4 analogues of thiolactomycin has been designed, synthesized and evaluated against four different species of *M. tuberculosis* namely *M. tuberculosis* H37Rv ATCC 27294, clinical isolates (sensitive and resistant), *M. avium* ATCC 49601 and *M. intracellulare* ATCC 13950. Of them some analogues have shown good activity against these strains with a MIC values in the range of 1.0-16 μg/mL (Kamal, A.; Shaik A. A.; Sinha, R.; Yadav, J. S.; Arora, S. K. *Bioorg. Med. Chem. Lett.* 2005, 15, 1927-1929.; Kamal, A.; Azeeza, S.; Malik, M. S.; Shaik, A. A.; Rao, M. V. *J. Pharm. Pharmaceut. Sci.* 2008, 11, 56s-80s.; Kamal, A.; Azeeza, S.; Malik, M. S. In *Drug resistant tuberculosis: Causes, Diagnosis and Treatments.* N'guy, S.; K'ung, Z. Eds.; Nova publishers: New York, 2009). The compounds mentioned in *J. Pharm. Pharmaceut. Sci.* 11 (2); 56s-80s, 2008 are same as mentioned in the journal *Bioorg. Med. Chem. Lett.* 2005, 1927-1929 and they have methyl group on piperazine ring system.

Compounds of Bioorg. Med. Chem. Lett. 2005, 1927-1929

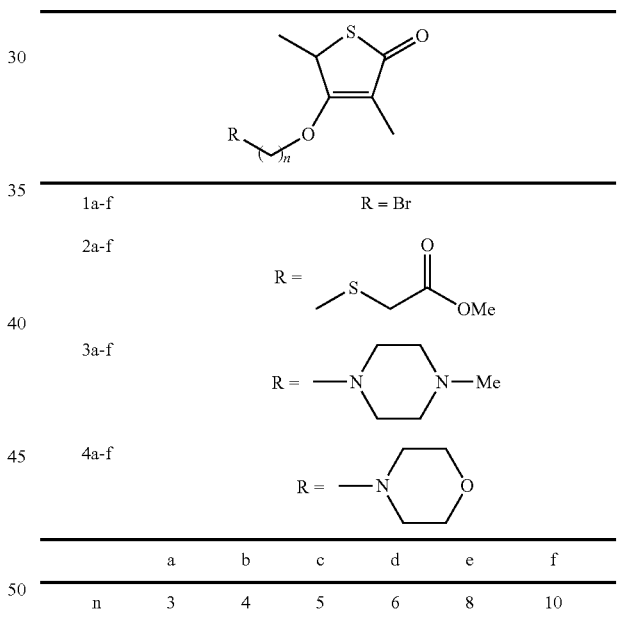

The results from previous studies encouraged us for the design, synthesis and evaluation of a library of new molecules based on thiolactomycin against sensitive and multi-drug resistant strains, which are presented in the present specification. The compounds of the present invention have quinoline ring system with different substituents on piperazine ring of thiolactone. The introduction of a quinoline ring system to the piperazine ring in the structures of present compounds results in a substantial increase in activity.

OBJECTIVE OF THE INVENTION

The main object of the invention is to provide the new quinolylpiperazino substituted compounds based on thiolactone as useful anti-tubercular antibiotics.

Another object of the present invention is to provide a process for the synthesis of these new quinolylpiperazino compounds of thiolactone as useful chemotherapeutic agent against latent, sensitive and MDR strains of TB.

Another object of the present invention is to provide target based anti-tubercular agents (FAS-II inhibitor) against latent, sensitive and MDR strains of tubercle bacilli.

Another object of the present invention is to provide new compounds based on the thiolactone and quinolylpiperazine in good yields.

SUMMARY OF THE INVENTION

Accordingly, the present invention relates to quinolylpiperazino substituted thiolactone compounds as anti-tubercular antibiotics and process for the preparation thereof. The present invention provides new class of C-4 quinolylpiperazino substituted compounds of thiolactone having the structural formula as follows.

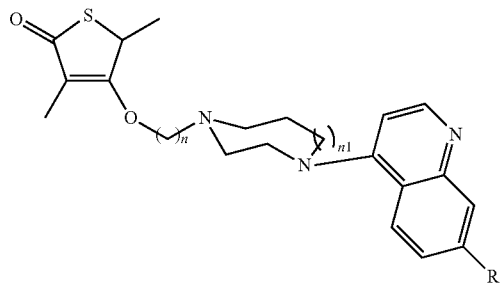

Formula A wherein,
n = 5-12
$n_1$ = 0, 1
R = $CF_3$ or Cl

In another embodiment of the present invention, Quinolylpiperazino substituted thiolactone compounds of general formulae A is represented by the compounds of general formulae 3a-f, 4a-f, 5a-f, 6a-f.

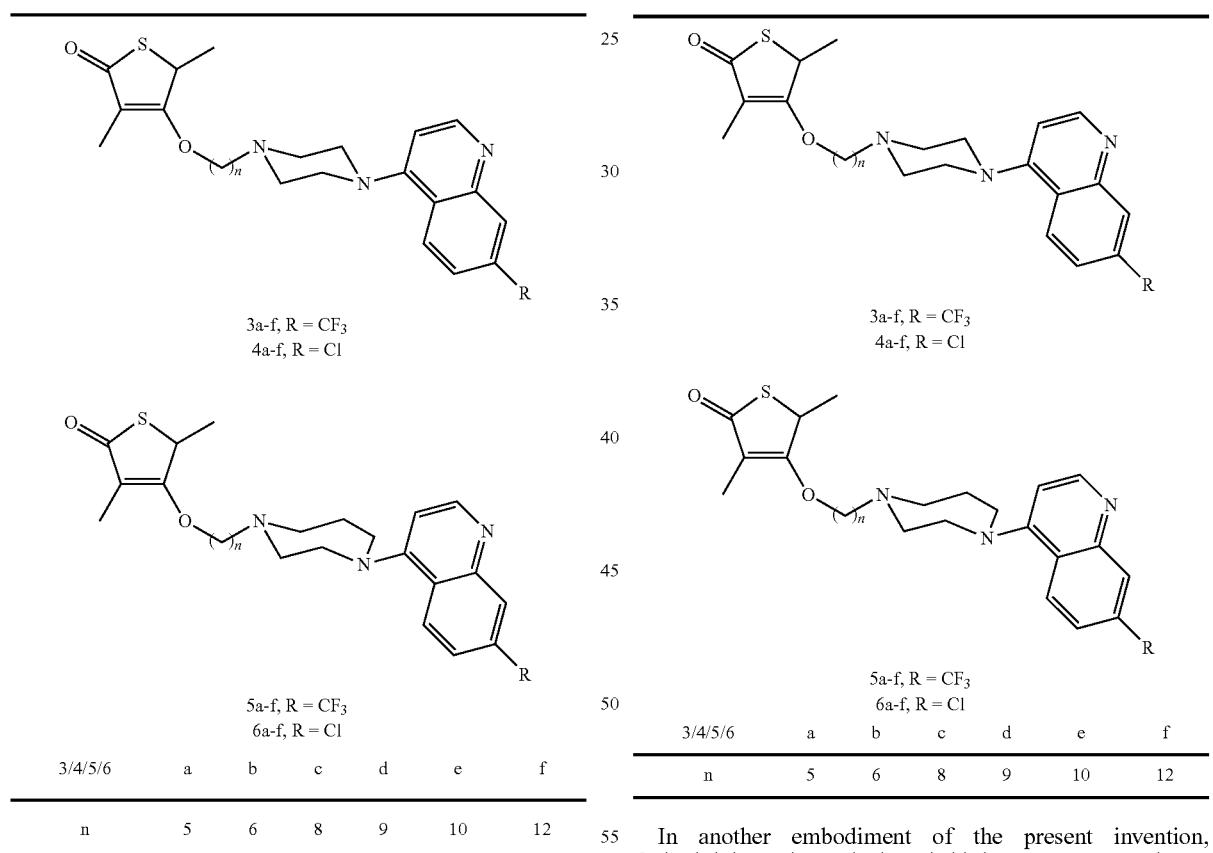

The present invention also provides a process for the preparation of new C-4 quinolylpiperazino substituted compounds of thiolactone as useful anti-tubercular agents. More particularly, it provides a process for the preparation of C-4 quinolylpiperazino compounds of thiolactone with systematic linking of alkane spacers.

In one embodiment of the present invention, Quinolylpiperazino substituted thiolactone compounds of general formulae A In another embodiment of the present invention, Quinolylpiperazino substituted thiolactone compounds are represented by the group of the following compounds:

3,5-dimethyl-4-[(5-4-[7-(trifluoromethyl)-4-quinolyl]piperazinopentyl)oxy]-5H-thiophen-2-one (3a).
3,5-dimethyl-4-[(6-4-[7-(trifluoromethyl)-4-quinolyl]piperazinohexyl)oxy]-5H-thiophen-2-one (3b)
3,5-dimethyl-4-[(8-4-[7-(trifluoromethyl)-4-quinolyl]piperazinooctyl)oxy]-5H-thiophen-2-one (3c).
3,5-dimethyl-4-[(9-4-[7-(trifluoromethyl)-4-quinolyl]piperazinononyl)oxy]-5H-thiophen-2-one (3d).
3,5-dimethyl-4-[(10-4-[7-(trifluoromethyl)-4-quinolyl]piperazinodecyl)oxy]-5H-thiophen-2-one (3e).

3,5-dimethyl-4-[(12-4-[7-(trifluoromethyl)-4-quinolyl]piperazinododecyl)oxy]-5H-thiophen-2-one (3f).
3,5-dimethyl-4-(5-[4-(7-chloro-4-quinolyl)piperazino]pentyloxy)-5H-thiophen-2-one (4a).
3,5-dimethyl-4-(6-[4-(7-chloro-4-quinolyl)piperazino]hexyloxy)-5H-thiophen-2-one (4b).
3,5-dimethyl-4-(8-[4-(7-chloro-4-quinolyl)piperazino]octyloxy)-5H-thiophen-2-one (4c).
3,5-dimethyl-4-(9-[4-(7-chloro-4-quinolyl)piperazino]nonyloxy)-5H-thiophen-2-one (4d).
3,5-dimethyl-4-(10-[4-(7-chloro-4-quinolyl)piperazino]decyloxy)-5H-thiophen-2-one (4e).
3,5-dimethyl-4-(12-[4-(7-chloro-4-quinolyl)piperazino]dodecyloxy)-5H-thiophen-2-one (4f).
3,5-dimethyl-4-[(5-4-[7-(trifluoromethyl)-4-quinolyl]-1,4-diazepan-1-ylpentyl)oxy]-5H-thiophen-2-one 5a).
3,5-dimethyl-4-[(6-4-[7-(trifluoromethyl)-4-quinolyl]-1,4-diazepan-1-ylhexyl)oxy]-5H-thiophen-2-one (5b).
3,5-dimethyl-4-[(8-4-[7-(trifluoromethyl)-4-quinolyl]-1,4-diazepan-1-yloctyl)oxy]-5H-thiophen-2-one (5c).
3,5-dimethyl-4-[(9-4-[7-(trifluoromethyl)-4-quinolyl]-1,4-diazepan-1-ylnonyl)oxy]-5H-thiophen-2-one (5d).
3,5-dimethyl-4-[(10-4-[7-(trifluoromethyl)-4-quinolyl]-1,4-diazepan-1-yldecyl)oxy]-5H-thiophen-2-one (5e).
3,5-dimethyl-4-[(12-4-[7-(trifluoromethyl)-4-quinolyl]-1,4-diazepan-1-yldodecyl)oxy]-5H-thiophen-2-one (5f).
3,5-dimethyl-4-(5-[4-(7-chloro-4-quinolyl)-1,4-diazepan-1-yl]pentyloxy)-5H-thiophen-2-one (6a).
3,5-dimethyl-4-(6-[4-(7-chloro-4-quinolyl)-1,4-diazepan-1-yl]hexyloxy)-5H-thiophen-2-one (6b).
3,5-dimethyl-4-(8-[4-(7-chloro-4-quinolyl)-1,4-diazepan-1-yl]octyloxy)-5H-thiophen-2-one (6c).
3,5-dimethyl-4-(9-[4-(7-chloro-4-quinolyl)-1,4-diazepan-1-yl]nonyloxy)-5H-thiophen-2-one (6d).
3,5-dimethyl-4-(10-[4-(7-chloro-4-quinolyl)-1,4-diazepan-1-yl]decyloxy)-5H-thiophen-2-one (6e).
3,5-dimethyl-4-(12-[4-(7-chloro-4-quinolyl)-1,4-diazepan-1-yl]dodecyloxy)-5H-thiophen-2-one (6f).

In another embodiment of the present invention, the structural formulae of the representative compounds are:

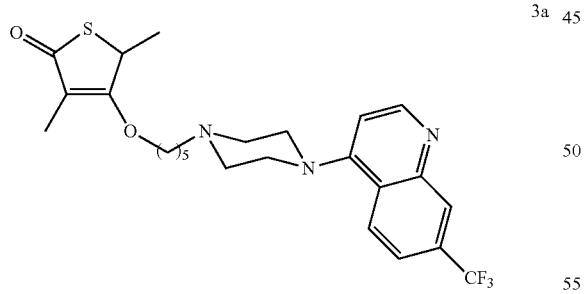

3a

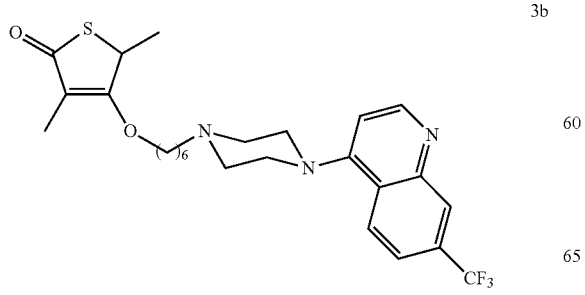

3b

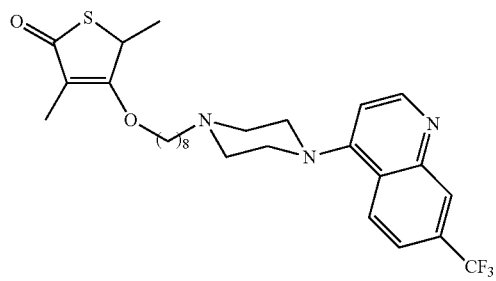

3c

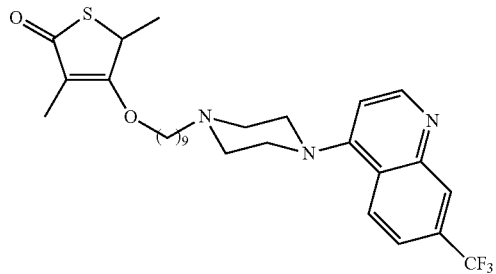

3d

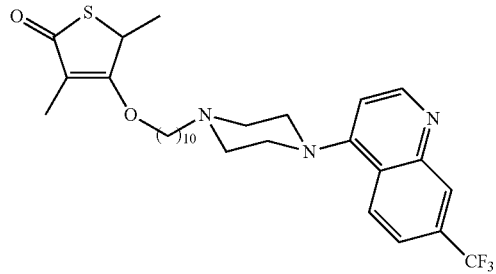

3e

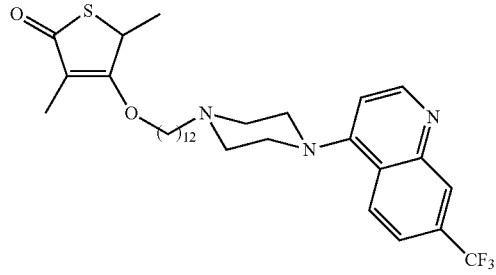

3f

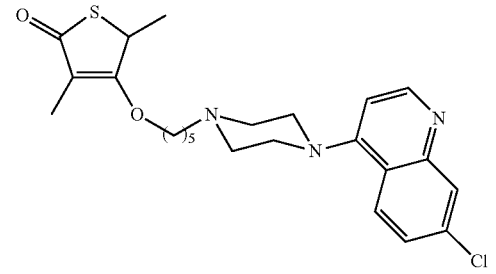

4a

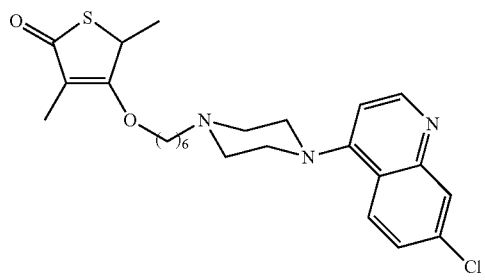
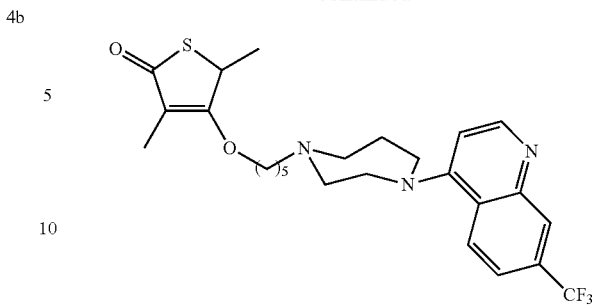

In another embodiment of the present invention, Quinolylpiperazino substituted thiolactone compounds of general formula A are useful as antitubercular agent.

In another embodiment of the present invention, compounds 3a-f, 4a-f, 5a-f and 6a-f exhibiting in vitro activity against *M. tuberculosis* H37Rv.

In another embodiment of the present invention, minimum inhibitory concentration (MIC) used for in vitro activity against *M. tuberculosis* H37Rv is in the range of 0.5-16 µg/ml respectively at an exposure period of at least 3 weeks.

In another embodiment of the present invention, the compound 3f exhibits in vitro activity against *M. tuberculosis* MDR-strains, *M. tuberculosis* XDR-strains and *Mycobacterium tuberculosis* H37Rv, CI.

In another embodiment of the present invention, compound 3f was not toxic on cell line AML-12 up to 100 µg/ml concentration.

In another embodiment of the present invention, a process for the preparation of Quinolylpiperazino substituted thiolactone compounds of general formulae A, Formula A wherein,
n = 5-12
$n_1$ = 0, 1
R = $CF_3$ or Cl wherein said process comprising the steps of
a. adding a base, dibromoalkane in the solution of 4-hydroxythiolactone in dry acetone in the mol ratio ranging between 4:2.5:1 to 4:4:1;

b. refluxing the reaction mixture as obtained in step (a) at temperature ranging between 55-60° C. for a period ranging between—36-48 h;
c. filtering the reaction mixture as obtained in step (b) followed by evaporating the solvent in vacuo to obtain crude product;
d. purifying the Crude product as obtained in step (c) by column chromatography pure bromoalkyl derivative of thiolactone;
e. adding bromoalkyl derivative of thiolactone as obtained in step (d), substituted 4-quinopiperazine/homopiperazine and a base in dry acetone followed by refluxing at temperature ranging between 55-60° C. for a period ranging between 36-48 h;
f. filtering the reaction mixture as obtained in step (e) to obtain crude product;
g. purifying the crude product as obtained in step (f) by column chromatography using ethyl acetate:hexane (7:3) as eluent to obtain pure quinolylpiperazino substituted thiolactone compounds.

In another embodiment of the present invention, dibromoalkane used in step (a) is selected from the group consisting of 1,5-dibromopentane, 1,6-dibromohexane, 1,8-dibromooctane, 1,9-dibromononane, 1,10-dibromodecane and 1,12-dibromododecane.

In another embodiment of the present invention, substituted -4-quinopiperazine/homopiperazine used in step (e) is selected from the group consisting of 7-trifluoromethyl-4-quinolylpiperazine, 7-chloro-4-quinolylpiperazine, 7-trifluoromethyl-4-quinolylhomopiperazine and -chloro-4-quinolylhomopiperazine.

In another embodiment of the present invention, base used in step (a) and (e) is selected from the group consisting of $K_2CO_3$ and triethylamine.

In another embodiment of the present invention, yield of quinolylpiperazino substituted thiolactone compounds is in the range of 70-90%.

BRIEF DESCRIPTION OF THE ACCOMPANYING DRAWINGS

Scheme 1: showing preparation of Quinolylpiperazino substituted thiolactone compounds
Scheme 2: showing preparation of substituted -4-quinopiperazine/homopiperazine
FIG. 1: In vivo efficacy of compound 3f against *Mycobacterium tuberculosis*.

DETAILED DESCRIPTION

The process for the synthesis of new thiolactone based compounds as anti-tubercular agents produces the novel compounds of the thiolactone in good yields, wherein the key step for the synthesis of these analogues is by direct nucleophilic substitution of 4-bromoalkoxythiolactone intermediates. The 4-bromoalkoxythiolactone, which has been reacted with substituted quinolylpiperazine or homopiperazines to afford the quinolylpiperazino/homopiperazino compounds of thiolactone.

These 4-bromoalkoxythiolactone intermediates have been prepared by the coupling of dibromoalkanes of varying chain lengths with 4-hydroxythiolactone as described in the literature (Kamal, A.; Shaik A. A.; Sinha, R.; Yadav, J. S.; Arora, S. K. *Bioorg. Med. Chem. Lett.* 2005, 15, 1927-1929).

Thus the present invention provides new class of thiolactone based derivatives, which were synthesized in a nucleophilic substituted manner.

A program was initiated in the laboratory for the design and synthesis of new thiolactone based compounds with enhanced anti-tubercular activity against sensitive and MDR-resistant strains. In these efforts new quinolylpiperazino substituted thiolactone based compounds have been synthesized and evaluated for their cytotoxicity and anti-tubercular potency compared to isoniazid. The synthesis of these compounds has been carried out as described in the Scheme-1 using 4-hydroxythiolactone as starting material.

Some of the compounds of the present invention are given below:
3a). 3,5-dimethyl-4-[(5-4-[7-(trifluoromethyl)-4-quinolyl]piperazinopentyl)oxy]-5H-thiophen-2-one
3b). 3,5-dimethyl-4-[(6-4-[7-(trifluoromethyl)-4-quinolyl]piperazinohexyl)oxy]-5H-thiophen-2-one
3c). 3,5-dimethyl-4-[(8-4-[7-(trifluoromethyl)-4-quinolyl]piperazinooctyl)oxy]-5H-thiophen-2-one
3d). 3,5-dimethyl-4-[(9-4-[7-(trifluoromethyl)-4-quinolyl]piperazinononyl)oxy]-5H-thiophen-2-one
3e). 3,5-dimethyl-4-[(10-4-[7-(trifluoromethyl)-4-quinolyl]piperazinodecyl)oxy]-5H-thiophen-2-one
3f). 3,5-dimethyl-4-[(12-4-[7-(trifluoromethyl)-4-quinolyl]piperazinododecyl)oxy]-5H-thiophen-2-one
4a). 3,5-dimethyl-4-(5-[4-(7-chloro-4-quinolyl)piperazino]pentyloxy)-5H-thiophen-2-one
4b). 3,5-dimethyl-4-(6-[4-(7-chloro-4-quinolyl)piperazino]hexyloxy)-5H-thiophen-2-one
4c). 3,5-dimethyl-4-(8-[4-(7-chloro-4-quinolyl)piperazino]octyloxy)-5H-thiophen-2-one
4d). 3,5-dimethyl-4-(9-[4-(7-chloro-4-quinolyl)piperazino]nonyloxy)-5H-thiophen-2-one
4e). 3,5-dimethyl-4-(10-[4-(7-chloro-4-quinolyl)piperazino]decyloxy)-5H-thiophen-2-one
4f). 3,5-dimethyl-4-(12-[4-(7-chloro-4-quinolyl)piperazino]dodecyloxy)-5H-thiophen-2-one
5a). 3,5-dimethyl-4-[(5-4-[7-(trifluoromethyl)-4-quinolyl]-1,4-diazepan-1-ylpentyl)oxy]-5H-thiophen-2-one
5b). 3,5-dimethyl-4-[(6-4-[7-(trifluoromethyl)-4-quinolyl]-1,4-diazepan-1-ylhexyl)oxy]-5H-thiophen-2-one
5c). 3,5-dimethyl-4-[(8-4-[7-(trifluoromethyl)-4-quinolyl]-1,4-diazepan-1-yloctyl)oxy]-5H-thiophen-2-one
5d). 3,5-dimethyl-4-[(9-4-[7-(trifluoromethyl)-4-quinolyl]-1,4-diazepan-1-ylnonyl)oxy]-5H-thiophen-2-one
5e). 3,5-dimethyl-4-[(10-4-[7-(trifluoromethyl)-4-quinolyl]-1,4-diazepan-1-yldecyl)oxy]-5H-thiophen-2-one
5f). 3,5-dimethyl-4-[(12-4-[7-(trifluoromethyl)-4-quinolyl]-1,4-diazepan-1-yldodecyl)oxy]-5H-thiophen-2-one
6a). 3,5-dimethyl-4-(5-[4-(7-chloro-4-quinolyl)-1,4-diazepan-1-yl]pentyloxy)-5H-thiophen-2-one
6b). 3,5-dimethyl-4-(6-[4-(7-chloro-4-quinolyl)-1,4-diazepan-1-yl]hexyloxy)-5H-thiophen-2-one
6c). 3,5-dimethyl-4-(8-[4-(7-chloro-4-quinolyl)-1,4-diazepan-1-yl]octyloxy)-5H-thiophen-2-one
6d). 3,5-dimethyl-4-(9-[4-(7-chloro-4-quinolyl)-1,4-diazepan-1-yl]nonyloxy)-5H-thiophen-2-one
6e). 3,5-dimethyl-4-(10-[4-(7-chloro-4-quinolyl)-1,4-diazepan-1-yl]decyloxy)-5H-thiophen-2-one
6f). 3,5-dimethyl-4-(12-[4-(7-chloro-4-quinolyl)-1,4-diazepan-1-yl]dodecyloxy)-5H-thiophen-2-one

EXAMPLES

The following examples are given by way of illustration and therefore should not be construed to the present limit of the scope of invention.

Example 1

3,5-dimethyl-4-[(5-4-[7-(trifluoromethyl)-4-quinolyl]piperazinopentyl)oxy]-5H-thiophen-2-one (3a)

To a solution of 4-hydroxy thiolactone (1.44 gm, 10 mmol) in dry acetone (25 mL), potassium carbonate (5.52 gm, 40 mmol) and 1,5-dibromopentane (9.2 gm, 40 mmol) were added and refluxed at 60° C. under $CaCl_2$ protection for 48 hours. This reaction mixture was filtered through celite, and the solution was evaporated in vacuo. The crude product thus obtained was further purified by column chromatography. The obtained pure bromopentyl derivative of thiolactone (293 mg, 1 mmol) was used for the next reaction. This step was carried out by adding 7-trifluoromethyl-4-quinolyl)piperazine (365 mg, 1.3 mmol), and potassium carbonate (553 mg, 4 mmol) in dry acetone under reflux conditions at 60° C. for 48 hours. Thus the reaction mixtures was filtered, and purified via column chromatography using ethyl acetate/hexane mixture (7:3) as eluent to get pure product in 80% yield.

$^1$H NMR (300 MHz; $CDCl_3$) δ 1.20-1.52 (6H, m), 1.59 (3H, d, J=7.3 Hz), 1.86 (3H, s), 2.61 (2H, t, J=7.3 Hz), 2.74-2.84 (4H, m), 3.22-3.35 (4H, m), 4.16-4.41 (3H, m), 6.96 (1H, d, J=4.5 Hz), 7.67 (1H, d, J=9.0 Hz), 8.13 (1H, J=9.0 Hz), 8.38 (1H, s), 8.85 (1H, d, J=4.5 Hz).

IR(KBr) cm$^{-1}$: 2936, 2858, 1679, 1626, 1585, 1458, 1382.
MS (ESI): 494 [M$^+$].

Example 2

3,5-dimethyl-4-[(6-4-[7-(trifluoromethyl)-4-quinolyl]piperazinohexyl)oxy]-5H-thiophen-2-one (3b)

This compound was prepared according to the method described for 3a by employing 1,6-dibromohexane (9.76 gm, 40 mmol), potassium carbonate (5.52 gm, 40 mmol), 4-hydroxythiolactone (1.44 gm, 10 mmol) in the first step and 7-trifluoromethyl-4-quinolylpiperazine (365 mg, 1.3 mmol), potassium carbonate (553 mg, 4 mmol) and bromohexyl derivative of thiolactone (307 mg, 1 mmol) in the next step to afford pure product in 84% yield.

$^1$H NMR (300 MHz; $CDCl_3$) δ 1.18-1.56 (8H, m), 1.59 (3H, d, J=7.3 Hz), 1.86 (3H, s), 2.53 (2H, t, J=7.3 Hz), 2.76-2.86 (4H, m), 3.26-3.36 (4H, m), 4.17-4.40 (3H, m), 6.95 (1H, d, J=4.5 Hz), 7.65 (1H, d, J=9.0 Hz), 8.12 (1H, J=9.0 Hz), 8.36 (1H, s), 8.81 (1H, d, J=4.5 Hz).

IR(KBr) cm$^{-1}$: 2936, 2857, 1678, 1626, 1583, 1458, 1382.
MS (ESI): 508 [M$^+$].

Example 3

3,5-dimethyl-4-[(8-4-[7-(trifluoromethyl)-4-quinolyl]piperazinooctyl)oxy]-5H-thiophen-2-one (3c)

This compound was prepared according to the method described for 3a by employing 1,8-dibromooctane (8.16 gm, 30 mmol), potassium carbonate (5.52 gm, 40 mmol), 4-hydroxythiolactone (1.44 gm, 10 mmol) in the first step and 7-trifluoromethyl-4-quinolylpiperazine (365 mg, 1.3 mmol), potassium carbonate (553 mg, 4 mmol) and bromooctyl derivative of thiolactone (335 mg, 1 mmol) in the next step to get pure product in 85% yield.

$^1$H NMR (300 MHz; $CDCl_3$) δ 1.19-1.52 (12H, m), 1.59 (3H, d, J=7.3 Hz), 1.85 (3H, s), 2.71 (2H, t, J=7.3 Hz), 2.93-3.08 (4H, m), 3.35-3.43 (4H, m), 4.15-4.42 (3H, m), 6.98 (1H, d, J=4.5 Hz), 7.66 (1H, d, J=8.3 Hz), 8.10 (1H, J=8.3 Hz), 8.37 (1H, s), 8.84 (1H, d, J=4.5 Hz).

IR(KBr) cm$^{-1}$: 2932, 2856, 1679, 1628, 1584, 1459, 1381.
MS (ESI): 536 [M$^+$].

Example 4

3,5-dimethyl-4-[(9-4-[7-(trifluoromethyl)-4-quinolyl]piperazinononyl)oxy]-5H-thiophen-2-one (3d)

This compound was prepared according to the method described for 3a by employing 1,9-dibromononane (8.58 gm, 30 mmol), potassium carbonate (5.52 gm, 40 mmol), 4-hydroxythiolactone (1.44 gm, 10 mmol) in the first step and 7-trifluoromethyl-4-quinolylpiperazine (365 mg, 1.3 mmol), potassium carbonate (553 mg, 4 mmol) and bromononyl derivative of thiolactone (349 mg, 1 mmol) in the next step to afford pure product in 86% yield.

$^1$H NMR (300 MHz; $CDCl_3$) δ 1.10-1.50 (14H, m), 1.59 (3H, d, J=7.3 Hz), 1.85 (3H, s), 2.76 (2H, t, J=7.3 Hz), 2.98-3.22 (4H, m), 3.36-3.52 (4H, m), 4.04-4.44 (3H, m), 6.99 (1H, d, J=4.5 Hz), 7.67 (1H, d, J=9.0 Hz), 8.08 (1H, J=9.0 Hz), 8.39 (1H, s), 8.85 (1H, d, J=4.5 Hz).

IR(KBr) cm$^{-1}$: 2932, 2856, 1677, 1624, 1586, 1459, 1382.
MS (ESI): 550 [M$^+$].

Example 5

3,5-dimethyl-4-[(10-4-[7-(trifluoromethyl)-4-quinolyl]piperazinodecyl)oxy]-5H-thiophen-2-one (3e)

This compound was prepared according to the method described for 3a by employing 1,10-dibromodecane (7.5 gm, 25 mmol), potassium carbonate (5.52 gm, 40 mmol), 4-hydroxythiolactone (1.44 gm, 10 mmol) in the first step and 7-trifluoromethyl-4-quinolylpiperazine (365 mg, 1.3 mmol), potassium carbonate (553 mg, 4 mmol) and bromodecyl derivative of thiolactone (363 mg, 1 mmol) in the next step to get pure product in 88% yield.

$^1$H NMR (300 MHz; $CDCl_3$) δ 1.08-1.52 (16H, m), 1.59 (3H, d, J=7.3 Hz), 1.87 (3H, s), 2.61 (2H, t, J=7.3 Hz), 2.88-3.20 (4H, m), 3.26-3.48 (4H, m), 4.08-4.42 (3H, m), 6.99 (1H, d, J=4.5 Hz), 7.65 (1H, d, J=9.0 Hz), 8.11 (1H, d, J=9.0 Hz), 8.38 (1H, s), 8.82 (1H, d, J=4.5 Hz).

IR(KBr) cm$^{-1}$: 2927, 2855, 1678, 1624, 1585, 1458, 1382.
MS (ESI): 564 [M$^+$].

Example 6

3,5-dimethyl-4-[(12-4-[7-(trifluoromethyl)-4-quinolyl]piperazinododecyl)oxy]-5H-thiophen-2-one (3l)

This compound was prepared according to the method described for 3a by employing 1,12-dibromododecane (8.2 gm, 25 mmol), potassium carbonate (5.52 gm, 40 mmol), 4-hydroxythiolactone (1.44 gm, 10 mmol) in the first step and 7-trifluoromethyl-4-quinolylpiperazine (365 mg, 1.3 mmol), potassium carbonate (553 mg, 4 mmol) and bromododecyl derivative of thiolactone (391 mg, 1 mmol) in the next step to afford pure product in 90% yield.

$^1$H NMR (200 MHz; $CDCl_3$) δ 1.04-1.54 (20H, m), 1.58 (3H, d, J=7.3 Hz), 1.85 (3H, s), 2.49 (2H, t, J=7.3 Hz), 2.70-2.84 (4H, m), 3.22-3.40 (4H, m), 4.02-4.48 (3H, m), 6.94 (1H, d, J=4.5 Hz), 7.64 (1H, d, J=8.7 Hz), 8.13 (1H, d, J=8.7 Hz), 8.35 (1H, s), 8.80 (1H, d, J=4.5 Hz).
$^{13}$C NMR (CDCl$_3$): δ 8.94, 19.77, 21.91, 24.62, 25.48, 26.23, 26.77, 29.08, 29.29, 29.76, 41.95, 46.14, 49.83, 52.22, 57.95, 62.55, 71.21, 110.72, 110.93, 113.74, 121.36, 121.56, 122.74, 124.45, 124.60, 127.48, 131.06, 148.18, 152.0, 155.36, 178.40, 196.10.
IR(KBr) cm$^{-1}$: 2935, 2859, 1676, 1627, 1582, 1457, 1383.
HRMS: 592.3169.

Example 7

3,5-dimethyl-4-(5-[4-(7-chloro-4-quinolyl)piperazino]pentyloxy)-5H-thiophen-2-one (4a)

This compound was prepared according to the method described for 3a by employing 1,5-dibromopentane (9.2 gm, 40 mmol), potassium carbonate (5.52 gm, 40 mmol), 4-hydroxythiolactone (1.44 gm, 10 mmol) in the first step and 7-chloro-4-quinolylpiperazine (322 mg, 1.3 mmol), potassium carbonate (553 mg, 4 mmol) and bromopentyl derivative of thiolactone (293 mg, 1 mmol) in the next step to get pure product in 75% yield.
$^1$H NMR (200 MHz; CDCl$_3$) δ 1.14-1.54 (6H, m), 1.58 (3H, d, J=7.3 Hz), 1.84 (3H, s), 2.51 (2H, t, J=7.3 Hz), 2.70-2.84 (4H, m), 3.14-3.34 (4H, m), 4.0-4.44 (3H, m), 6.83 (1H, d, J=4.5 Hz), 7.39 (1H, d, J=9.0 Hz), 7.88 (1H, d, J=9.0 Hz), 8.03 (1H, s); 8.70 (1H, d, J=4.5 Hz).
IR(KBr) cm$^{-1}$: 2933, 2857, 1677, 1626, 1572, 1498, 1454, 1379.
MS (ESI): 460 [M$^+$].

Example 8

3,5-dimethyl-4-(6-[4-(7-chloro-4-quinolyl)piperazino]hexyloxy)-5H-thiophen-2-one (4b)

This compound was prepared according to the method described for 3a by employing 1,6-dibromohexane (9.76 gm, 40 mmol), potassium carbonate (5.52 gm, 40 mmol), 4-hydroxythiolactone (1.44 gm, 10 mmol) in the first step and 7-chloro-4-quinolylpiperazine (322 mg, 1.3 mmol), potassium carbonate (553 mg, 4 mmol) and bromohexyl derivative of thiolactone (307 mg, 1 mmol) in the next step to afford pure product in 78% yield.
$^1$H NMR (300 MHz; CDCl$_3$) δ 1.22-1.55 (8H, m), 1.58 (3H, d, J=7.3 Hz), 1.83 (3H, s), 2.45 (2H, t, J=7.3 Hz), 2.66-2.76 (4H, m), 3.16-3.26 (4H, m), 4.03-4.39 (3H, m), 6.80 (1H, d, J=4.5 Hz), 7.37 (1H, d, J=9.0 Hz), 7.89 (1H, d, J=9.0 Hz), 8.0 (1H, s), 8.66 (1H, d, J=4.5 Hz).
IR(KBr) cm$^{-1}$: 2932, 2857, 1676, 1627, 1572, 1497, 1453, 1378.
HRMS: 474.1979.

Example 9

3,5-dimethyl-4-(8-[4-(7-chloro-4-quinolyl)piperazino]octyloxy)-5H-thiophen-2-one (4c)

This compound was prepared according to the method described for 3a by employing 1,8-dibromooctane (8.16 gm, 30 mmol), potassium carbonate (5.52 gm, 40 mmol), 4-hydroxythiolactone (1.44 gm, 10 mmol) in the first step and 7-chloro-4-quinolylpiperazine (322 mg, 1.3 mmol), potassium carbonate (553 mg, 4 mmol) and bromooctyl derivative of thiolactone (335 mg, 1 mmol) in the next step to get pure product in 79% yield.
$^1$H NMR (300 MHz; CDCl$_3$) δ 1.28-1.54 (12H, m), 1.58 (3H, d, J=7.3 Hz), 1.84 (3H, s), 2.44 (2H, t, J=7.3 Hz), 2.67-2.76 (4H, m), 3.18-3.28 (4H, m), 4.05-4.34 (3H, m), 6.81 (1H, d, J=4.5 Hz), 7.38 (1H, d, J=9.0 Hz), 7.90 (1H, d, J=9.0 Hz), 8.0 (1H, s), 8.68 (1H, d, J=4.5 Hz).
IR(KBr) cm$^{-1}$: 2934, 2858, 1677, 1628, 1572, 1498, 1455, 1380.
HRMS: 502.2273.

Example 10

3,5-dimethyl-4-(9-[4-(7-chloro-4-quinolyl)piperazino]nonyloxy)-5H-thiophen-2-one (4d)

This compound was prepared according to the method described for 3a by employing 1,9-dibromononane (8.58 gm, 30 mmol), potassium carbonate (5.52 gm, 40 mmol), 4-hydroxythiolactone (1.44 gm, 10 mmol) in the first step and 7-chloro-4-quinolylpiperazine (322 mg, 1.3 mmol), potassium carbonate (553 mg, 4 mmol) and bromononyl derivative of thiolactone (349 mg, 1 mmol) in the next step to get pure product in 80% yield.
$^1$H NMR (300 MHz; CDCl$_3$) δ 1.22-1.52 (14H, m), 1.58 (3H, d, J=7.3 Hz), 1.84 (3H, s), 2.43 (2H, t, J=7.3 Hz), 2.66-2.76 (4H, m), 3.10-3.28 (4H, m), 4.05-4.35 (3H, m), 6.80 (1H, d, J=4.5 Hz), 7.38 (1H, d, J=9.0 Hz), 7.90 (1H, d, J=9.0 Hz), 8.0 (1H, s), 8.67 (1H, d, J=4.5 Hz).
IR(KBr) cm$^{-1}$: 2932, 2856, 1676, 1629, 1574, 1499, 1454, 1381.
HRMS: 516.2423.

Example 11

3,5-dimethyl-4-(10-[4-(7-chloro-4-quinolyl)piperazino]decyloxy)-5H-thiophen-2-one (4e)

This compound was prepared according to the method described for 3a by employing 1,10-dibromodecane (7.5 gm, 25 mmol), potassium carbonate (5.52 gm, 40 mmol), 4-hydroxythiolactone (1.44 gm, 10 mmol) in the first step and 7-chloro-4-quinolylpiperazine (322 mg, 1.3 mmol), potassium carbonate (553 mg, 4 mmol) and bromodecyl derivative of thiolactone (363 mg, 1 mmol) in the next step to get pure product in 83% yield.
$^1$H NMR (300 MHz; CDCl$_3$) δ 1.20-1.54 (16H, m), 1.57 (3H, d, J=7.3 Hz), 1.82 (3H, s), 2.43 (2H, t, J=7.3 Hz), 2.64-2.76 (4H, m), 3.15-3.29 (4H, m), 4.02-4.36 (3H, m), 6.80 (1H, d, J=4.5 Hz), 7.37 (1H, d, J=9.0 Hz), 7.90 (1H, d, J=9.0 Hz), 8.0 (1H, s), 8.66 (1H, d, J=4.5 Hz).
IR(KBr) cm$^{-1}$: 2926, 2853, 1679, 1629, 1573, 1498, 1456, 1378.
HRMS: 530.2592.

Example 12

3,5-dimethyl-4-(12-[4-(7-chloro-4-quinolyl)piperazino]dodecyloxy)-5H-thiophen-2-one (4f)

This compound was prepared according to the method described for 3a by employing 1,12-dibromododecane (8.2 gm, 25 mmol), potassium carbonate (5.52 gm, 40 mmol), 4-hydroxythiolactone (1.44 gm, 10 mmol) in the first step and 7-chloro-4-quinolylpiperazine (322 mg, 1.3 (mmol), potassium carbonate (553 mg, 4 mmol) and bromododecyl derivative of thiolactone (391 mg, 1 mmol) in the next step to get pure product in 85% yield.

¹H NMR (200 MHz; CDCl₃) δ 1.18-1.48 (20H, m), 1.56 (3H, d, J=7.3 Hz), 1.82 (3H, s), 2.44 (2H, t, J=7.3 Hz), 2.60-2.80 (4H, m), 3.13-3.31 (4H, m), 3.98-4.37 (3H, m), 6.80 (1H, d, J=4.5 Hz), 7.36 (1H, d, J=9.0 Hz), 7.89 (1H, d, J=9.0 Hz), 8.0 (1H, s), 8.66 (1H, d, J=4.5 Hz).
IR(KBr) cm⁻¹: 2926, 2852, 1678, 1628, 1573, 1497; 1455, 1379.
HRMS: 558.2904.

Example 13

3,5-dimethyl-4-[(5-4-[7-(trifluoromethyl)-4-quinolyl]-1,4-diazepan-1-ylpentyl)oxy]-5H-thiophen-2-one (5a)

This compound was prepared according to the method described for 3a by employing 1,5-dibromopentane (9.2 gm, 40 mmol), potassium carbonate (5.52 gm, 40 mmol), 4-hydroxythiolactone (1.44 gm, 10 mmol) in the first step and 7-trifluoromethyl-4-quinolylhomopiperazine (384 mg, 1.3 mmol), potassium carbonate (553 mg, 4 mmol) and bromopentyl derivative of thiolactone (293 mg, 1 mmol) in the next step to get pure product in 70% yield.
¹H NMR (300 MHz; CDCl₃) δ 1.22-1.52 (6H, m), 1.58 (3H, d, J=7.3 Hz), 1.86 (3H, s), 2.29 (2H, m), 2.82 (2H, t, J=7.3 Hz), 3.09-3.22 (4H, m), 3.62-3.72 (4H, m), 4.04-4.38 (3H, m), 6.88 (1H, d, J=5.2 Hz), 7.62 (1H, d, J=9.0 Hz), 8.17 (1H, d, J=9.0 Hz), 8.35 (1H, s), 8.73 (1H, d, J=5.2 Hz).
IR(KBr) cm⁻¹: 2927, 2854, 1677, 1629, 1576, 1512, 1461, 1382.
MS (ESI): 508 [M⁺].

Example 14

3,5-dimethyl-4-[(6-4-[7-(trifluoromethyl)-4-quinolyl]-1,4-diazepan-1-ylhexyl)oxy]-5H-thiophen-2-one (5b)

This compound was prepared according to the method described for 3a by employing 1,6-dibromohexane (9.76 gm, 40 mmol), potassium carbonate (5.52 gm, 40 mmol), 4-hydroxythiolactone (1.44 gm, 10 mmol) in the first step and 7-trifluoromethyl-4-quinolylhomopiperazine (384 mg, 1.3 mmol), potassium carbonate (553 mg, 4 mmol) and bromohexyl derivative of thiolactone (307 mg, 1 mmol) in the next step to get pure product in 72% yield.
¹NMR (300 MHz; CDCl₃) δ 1.20-1.53 (8H, m), 1.58 (3H, d, J=7.3 Hz), 1.86 (3H, s), 2.28 (2H, m), 2.83 (2H, t, J=7.3 Hz), 3.08-3.24 (4H, m), 3.62-3.74 (4H, m), 4.08-4.41 (3H, m), 6.89 (1H, d, J=5.2 Hz), 7.58 (1H, d, J=9.0 Hz), 8.16 (1H, d, J=9.0 Hz), 8.32 (1H, s), 8.72 (1H, d, J=5.2 Hz).
IR(KBr) cm⁻¹: 2927, 2853, 1679, 1628, 1575, 1513, 1460, 1383.
MS (ESI): 522 [M⁺].

Example 15

3,5-dimethyl-4-[(8-4-[7-(trifluoromethyl)-4-quinolyl]-1,4-diazepan-1-yloctyl)oxy]-5H-thiophen-2-one (5c)

This compound was prepared according to the method described for 3a by employing 1,8-dibromooctane (8.16 gm, 30 mmol), potassium carbonate (5.52 gm, 40 mmol), 4-hydroxythiolactone (1.44 gm, 10 mmol) in the first step and 7-trifluoromethyl-4-quinolylhomopiperazine (384 mg, 1.3 mmol), potassium carbonate (553 mg, 4 mmol) and bromooctyl derivative of thiolactone (335 mg, 1 mmol) in the next step to get pure product in 76% yield.
¹NMR (300 MHz; CDCl₃) δ 1.18-1.51 (12H, m), 1.58 (3H, d, J=7.3 Hz), 1.85 (3H, s), 2.18 (2H, m), 2.85 (2H, t, J=7.3 Hz), 3.07-3.25 (4H, m), 3.61-3.78 (4H, m), 4.08-4.39 (3H, m), 6.88 (1H, d, J=5.2 Hz), 7.59 (1H, d, J=9.0 Hz), 8.11 (1H, d, J=9.0 Hz), 8.35 (1H, s), 8.69 (1H, d, J=5.2 Hz).
IR(KBr) cm⁻¹: 2926, 2851, 1677, 1626, 1576, 1510, 1458, 1380.
MS (ESI): 550 [M⁺].

Example 16

3,5-dimethyl-4-[(9-4-[7-(trifluoromethyl)-4-quinolyl]-1,4-diazepan-1-ylnonyl)oxy]-5H-thiophen-2-one (5d)

This compound was prepared according to the method described for 3a by employing 1,9-dibromononane (8.58 gm, 30 mmol), potassium carbonate (5.52 gm, 40 mmol), 4-hydroxythiolactone (1.44 gm, 10 mmol) in the first step and 7-trifluoromethyl-4-quinolylhomopiperazine (384 mg, 1.3 mmol), potassium carbonate (553 mg, 4 mmol) and bromononyl derivative of thiolactone (349 mg, 1 mmol) in the next step to afford pure product in 80% yield.
¹NMR (300 MHz; CDCl₃) δ 1.10-1.51 (14H, m), 1.58 (3H, d, J=7.3 Hz), 1.84 (3H, s), 2.23 (2H, m), 2.82 (2H, t, J=7.3 Hz), 3.08-3.27 (4H, m), 3.60-3.84 (4H, m), 4.08-4.40 (3H, m), 6.89 (1H, d, J=5.2 Hz), 7.62 (1H, d, J=9.0 Hz), 8.09 (1H, d, J=9.0 Hz), 8.33 (1H, s), 8.72 (1H, d, J=5.2 Hz).
IR(KBr) cm⁻¹: 2928, 2852, 1678, 1629, 1576, 1511, 1458, 1381.
MS (ESI): 564 [M⁺].

Example 17

3,5-dimethyl-4-[(10-4-[7-(trifluoromethyl)-4-quinolyl]-1,4-diazepan-1-yldecyl)oxy]-5H-thiophen-2-one (5e)

This compound was prepared according to the method described for 3a by employing 1,10-dibromodecane (7.5 gm, 25 mmol), potassium carbonate (5.52 gm, 40 mmol), 4-hydroxythiolactone (1.44 gm, 10 mmol) in the first step and 7-trifluoromethyl-4-quinolylhomopiperazine (384 mg, 1.3 mmol), potassium carbonate (553 mg, 4 mmol) and bromodecyl derivative of thiolactone (363 mg, 1 mmol) in the next step to get pure product in 84% yield.
¹H NMR (300 MHz; CDCl₃) δ 1.15-1.56 (16H, m), 1.58 (3H, d, J=7.3 Hz), 1.84 (3H, s), 2.08 (2H, m), 2.54 (2H, t, J=7.3 Hz), 2.78-2.94 (4H, m), 3.58-3.72 (4H, m), 4.05-4.38 (3H, m), 6.82 (1H, d, J=5.2 Hz), 7.57 (1H, d, J=9.0 Hz), 8.11 (1H, d, J=9.0 Hz), 8.29 (1H, s), 8.66 (1H, d, J=5.2 Hz).
IR(KBr) cm⁻¹: 2926, 2853, 1678, 1627, 1575, 1514, 1459, 1384.
MS (ESI): 578 [M⁺].

Example 18

3,5-dimethyl-4-[(12-4-[7-(trifluoromethyl)-4-quinolyl]-1,4-diazepan-1-yldodecyl)oxy]-5H-thiophen-2-one (5f)

This compound was prepared according to the method described for 3a by employing 1,12-dibromododecane (8.2 gm, 25 mmol), potassium carbonate (5.52 gm, 40 mmol), 4-hydroxythiolactone (1.44 gm, 10 mmol) in the first step and 7-trifluoromethyl-4-quinolylhomopiperazine (384 mg, 1.3 mmol), potassium carbonate (553 mg, 4 mmol) and bromododecyl derivative of thiolactone (391 mg, 1 mmol) in the next step to get pure product in 86% yield.

$^1$H NMR (300 MHz; CDCl$_3$) δ 1.18-1.56 (20H, m), 1.58 (3H, d, J=7.3 Hz), 1.85 (3H, s), 2.08 (2H, m), 2.53 (2H, t, J=7.3 Hz), 2.78-2.94 (4H, m), 3.61-3.73 (4H, m), 4.08-4.36 (3H, m), 6.83 (1H, d, J=5.2 Hz), 7.57 (1H, d, J=9.0 Hz), 8.12 (1H, d, J=9.0 Hz), 8.30 (1H, s), 8.67 (1H, d, J=5.2 Hz).

IR(KBr) cm$^{-1}$: 2927, 2853, 1679, 1628, 1575, 1513, 1460, 1383.

MS (ESI): 606 [M$^+$].

Example 19

3,5-dimethyl-4-(5-[4-(7-chloro-4-quinolyl)-1,4-diazepan-1-yl]pentyloxy)-5H-thiophen-2-one (6a)

This compound was prepared according to the method described for 3a by employing 1,5-dibromopentane (9.2 gm, 40 mmol), potassium carbonate (5.52 gm, 40 mmol), 4-hydroxythiolactone (1.44 gm, 10 mmol) in the first step and 7-chloro-4-quinolylhomopiperazine (341 mg, 1.3 mmol), potassium carbonate (553 mg, 4 mmol) and bromopentyl derivative of thiolactone (293 mg, 1 mmol) in the next step to get pure product in 72% yield.

$^1$; NMR (300 MHz; CDCl$_3$) δ 1.08-1.58 (6H, m), 1.55 (3H, d, J=7.5 Hz), 1.81 (3H, s), 2.21-2.33 (2H, m), 2.89 (2H, t, J=7.5 Hz), 3.16-3.40 (4H, m), 3.56-3.97 (4H, m), 4.08-4.36 (3H, m), 6.80 (1H, d, J=5.2 Hz), 7.38 (1H, d, J=9.0 Hz), 7.88 (1H, d, J=9.0 Hz), 8.0 (1H, s), 8.57 (1H, d, J=5.2 Hz).

IR(KBr) cm$^{-1}$: 2927, 2854, 1671, 1625, 1575, 1497, 1429, 1383.

MS (ESI): 474 [M$^+$].

Example 20

3,5-dimethyl-4-(6-[4-(7-chloro-4-quinolyl)-1,4-diazepan-1-yl]hexyloxy)-5H-thiophen-2-one (6b)

This compound was prepared according to the method described for 3a by employing 1,6-dibromohexane (9.76 gm, 40 mmol), potassium carbonate (5.52 gm, 40 mmol), 4-hydroxythiolactone (1.44 gm, 10 mmol) in the first step and 7-chloro-4-quinolylhomopiperazine (341 mg, 1.3 mmol), potassium carbonate (553 mg, 4 mmol) and bromohexyl derivative of thiolactone (307 mg, 1 mmol) in the next step to get pure product in 75% yield.

$^1$H NMR (300 MHz; CDCl$_3$) δ 1.08-1.58 (8H, m), 1.55 (3H, d, J=7.5 Hz), 1.81 (3H, s), 2.21-2.33 (2H, m), 2.89 (2H, t, J=7.5 Hz), 3.16-3.40 (4H, m), 3.56-3.97 (4H, m), 4.08-4.36 (3H, m), 6.80 (1H, d, J=5.2 Hz), 7.38 (1H, d, J=9.0 Hz), 7.88 (1H, d, J=9.0 Hz), 8.0 (1H, s), 8.57 (1H, d, J=5.2 Hz).

IR(KBr) cm$^{-1}$: 2925, 2854, 1673, 1625, 1567, 1499, 1428, 1382.

MS (ESI): 488 [M$^+$].

Example 21

3,5-dimethyl-4-(8-[4-(7-chloro-4-quinolyl)-1,4-diazepan-1-yl]octyloxy)-5H-thiophen-2-one (6c)

This compound was prepared according to the method described for 3a by employing 1,8-dibromooctane (8.16 gm, 30 mmol), potassium carbonate (5.52 gm, 40 mmol), 4-hydroxythiolactone (1.44 gm, 10 mmol) in the first step and 7-chloro-4-quinolylhomopiperazine (341 mg, 1.3 mmol), potassium carbonate (553 mg, 4 mmol) and bromooctyl derivative of thiolactone (335 mg, 1 mmol) in the next step to get pure product in 78% yield.

$^1$H NMR (300 MHz; CDCl$_3$) δ 1.08-1.58 (12H, m), 1.55 (3H, d, J=7.5 Hz), 1.81 (3H, s), 2.21-2.33 (2H, m), 2.89 (2H, t, J=7.5 Hz), 3.16-3.40 (4H, m), 3.56-3.97 (4H, m), 4.08-4.36 (3H, m), 6.80 (1H, d, J=5.2 Hz), 7.38 (1H, d, J=9.0 Hz), 7.88 (1H, d, J=9.0 Hz), 8.0 (1H, s), 8.57 (1H, d, J=5.2 Hz).

IR(KBr) cm$^{-1}$: 2926, 2852, 1676, 1624, 1569, 1499, 1426, 1384.

MS (ESI): 516 [M$^+$].

Example 22

3,5-dimethyl-4-(10-[4-(7-chloro-4-quinolyl)-1,4-diazepan-1-yl]nonyloxy)-5H-thiophen-2-one (6d)

This compound was prepared according to the method described for 3a by employing 1,9-dibromononane (8.58 gm, 30 mmol), potassium carbonate (5.52 gm, 40 mmol), 4-hydroxythiolactone (1.44 gm, 10 mmol) in the first step and 7-chloro-4-quinolylhomopiperazine (365 mg, 1.3 Mmol), potassium carbonate (553 mg, 4 mmol) and bromononyl derivative of thiolactone (349 mg, 1 mmol) in the next step to get pure product in 81% yield.

$^1$H NMR (300 MHz; CDCl$_3$) δ 1.08-1.58 (14H, m), 1.55 (3H, d, J=7.5 Hz), 1.81 (3H, s), 2.21-2.33 (2H, m), 2.89 (2H, t, J=7.5 Hz), 3.16-3.40 (4H, m), 3.56-3.97 (4H, m), 4.08-4.36 (3H, m), 6.80 (1H, d, J=5.2 Hz), 7.38 (1H, d, J=9.0 Hz), 7.88 (1H, d, J=9.0 Hz), 8.0 (1H, s), 8.57 (1H, d, J=5.2 Hz).

IR(KBr) cm$^{-1}$: 2928, 2854, 1674, 1625, 1568, 1498, 1428, 1381.

MS (ESI): 530 [M$^+$].

Example 23

3,5-dimethyl-4-(12-[4-(7-chloro-4-quinolyl)-1,4-diazepan-1-yl]decyloxy)-5H-thiophen-2-one (6e)

This compound was prepared according to the method described for 3a by employing 1,10-dibromodecane (7.5 gm, 25 mmol), potassium carbonate (5.52 gm, 40 mmol), 4-hydroxythiolactone (1.44 gm, 10 mmol) in the first step and 7-chloro-4-quinolylhomopiperazine (341 mg, 1.3 mmol), potassium carbonate (553 mg, 4 mmol) and bromodecyl derivative of thiolactone (363 mg, 1 mmol) in the next step to get pure product in 84% yield.

$^1$H NMR (300 MHz; CDCl$_3$) δ 1.20-1.50 (16H, m), 1.58 (3H, d, J=7.5 Hz), 1.85 (3H, s), 2.16-2.28 (2H, m), 2.77 (2H, t, J=7.5 Hz), 3.06-3.22 (4H, m), 3.60-3.86 (4H, m), 4.14-4.36 (3H, m), 6.79 (1H, d, J=5.2 Hz), 7.40 (1H, d, J=9.0 Hz), 7.90 (1H, d, J=9.0 Hz), 8.05 (1H, s), 8.63 (1H, d, J=5.2 Hz).

IR(KBr) cm$^{-1}$: 2927, 2852, 1676, 1627, 1571, 1499, 1429, 1383.

MS (ESI): 544 [M$^+$].

Example 24

3,5-dimethyl-4-(12-[4-(7-chloro-4-quinolyl)-1,4-diazepan-1-yl]dodecyloxy)-5H-thiophen-2-one (6f)

This compound was prepared according to the method described for 3a by employing 1,12-dibromododecane (8.2 gm, 25 mmol), potassium carbonate (5.52 gm, 40 mmol), 4-hydroxythiolactone (1.44 gm, 10 mmol) in the first step and 7-trifluoromethyl-4-quinolylpiperazine (341 mg, 1.3 mmol), potassium carbonate (553 mg, 4 mmol) and bromododecyl derivative of thiolactone (391 mg, 1 mmol) in the next step to get pure product in 85% yield.

$^1$H NMR (300 MHz; CDCl$_3$) δ 1.18-1.48 (20H, m), 1.58 (3H, d, J=7.5 Hz), 1.84 (3H, s), 2.12-2.25 (2H, m), 2.73 (2H, t, J=7.3 Hz), 3.0-3.18 (4H, m), 3.49-3.80 (4H, m), 4.05-4.38 (3H, m), 6.77 (1H, d, J=5.2 Hz), 7.38 (1H, d, J=9.0 Hz), 7.90 (1H, d, J=9.0 Hz), 8.02 (1H, s), 8.59 (1H, d, J=5.2 Hz).

IR(KBr) cm$^{-1}$: 2928, 2853, 1674, 1626, 1570, 1501, 1428, 1380.

HRMS: 572.3056.

Biological Studies

Example 25

In-Vitro Activity of Compound 3a to 6f Against *M. tuberculosis* H37Rv

MIC Determination:

MIC was determined by broth dilution method. *M. tuberculosis* H37Rv (ATCC 27294; American Type Culture Collection, Manassas, Va.) culture was grown for 10 to 15 days in Middlebrook 7H9 broth (Difco Laboratories, Detroit, Mich.) supplemented with 0.5% (v/v) glycerol, 0.25% (v/v) Tween 80 (Himedia, Mumbai India), and 10% ADC (albumin dextrose catalase, Becton Dickinson, Sparks, Md.) under shaking conditions at 37° C. in 5% CO$_2$ to facilitate exponential-phase growth of the organism. Bacterial suspension was prepared by suspending *M. tuberculosis* growth in normal saline containing 0.5% tween 80 and turbidity was adjusted to 1 McFarland standard which is equivalent to 1.5×10$^7$ CFU/ml. The 2-fold serial dilutions of compounds 3a to 6f were prepared in Middle brook 7H9 (Difco laboratories) for *M. tuberculosis* in 100 µl per well in 96-well U bottom microtitre plates (Tarson, Mumbai, India).

The above-mentioned bacterial suspension was further diluted in the growth media and 100 µl volume of this diluted inoculum was added to each well of the plate resulting in the final inoculum of 5×10$^5$ CFU/ml in the well.

The starting concentration of the compounds is 16 mg/ml. Two fold serial dilutions were made in microtitre plate. The dilutions were as follows: 16, 8, 4, 2, 1, 0.5, 0.25, 0.12 mg/ml. All the concentrations were inoculated with the test bacteria. Thus the final concentrations of compound 3a to 6f ranged from 0.12 to 16 µg/ml Minimum inhibitory concentration (MIC) was arrived at by observing the minimum concentration of the compound that inhibits the growth of bacteria. The plates were incubated at 37° C. for 3-weeks in 5% CO$_2$. The plates were read visually and the minimum concentration of the compound showing no turbidity was recorded as MIC. The introduction of a quinoline ring system to the piperazine ring in the structures of present compounds results in a substantial increase in activity. As seen in table 1 below, the MIC of the compounds of the present invention is quite low as compared to MIC of Thiolactomycin, which is 25.

Results:

TABLE 1

In vitro activity against M. tuberculosis H37Rv

| S. No | Compound | MIC (µg/mL) |
|---|---|---|
| 1 | 3a | 16 |
| 2 | 3b | 16 |
| 3 | 3c | 16 |
| 4 | 3d | 16 |
| 5 | 3e | 16 |
| 6 | 3f | 0.5 |
| 7 | 4a | 16 |
| 8 | 4b | 16 |
| 9 | 4c | 8 |
| 10 | 4d | 8 |
| 11 | 4e | 8 |
| 12 | 4f | 8 |
| 13 | 5a | 16 |
| 14 | 5b | 16 |
| 15 | 5c | 16 |
| 16 | 5d | 16 |
| 17 | 5e | 8 |
| 18 | 5f | 8 |
| 19 | 6a | 16 |
| 20 | 6b | 8 |
| 21 | 6c | 16 |
| 22 | 6d | 8 |
| 23 | 6e | 16 |
| 24 | 6f | 4 |

Isoniazid 0.5
Thiolactomycin 25

Example 26

MIC Determination of 3f Against *M. tuberculosis* Isolates

MIC determination: MIC was determined by broth dilution method. *M. tuberculosis* H37Rv (ATCC 27294; American Type Culture Collection, Manassas, Va.) culture was used throughout the studies along with *M. tuberculosis* 617 (MDR clinical isolate obtained from JALMA, Agra, India) and *M. tuberculosis* XDR-1 (XDR clinical isolate obtained from Religare, laboratories, Gurgaon, India). Cultures were grown for 10 to 15 days in Middlebrook 7H9 broth (Difco Laboratories, Detroit, Mich.) supplemented with 0.5% (v/v) glycerol, 0.25% (v/v) Tween 80 (Himedia, Mumbai India), and 10% ADC (albumin dextrose catalase, Becton Dickinson, Sparks, Md.) under shaking conditions at 37° C. in 5% CO$_2$ to facilitate exponential-phase growth of the organism. Bacterial suspension was prepared by suspending *M. tuberculosis* growth in normal saline containing 0.5% tween 80 and turbidity was adjusted to 1 McFarland standard which is equivalent to 1.5×10$^7$ CFU/ml. The 2-fold serial dilutions of compounds 3f were prepared in Middle brook 7H9 (Difco laboratories) for *M. tuberculosis* in 100 µl per well in 96-well U bottom microtitre plates (Tarson, Mumbai, India). The above-mentioned bacterial suspension was further diluted in the growth media and 100 µl volume of this diluted inoculum was added to each well of the plate resulting in the final inoculum of 5×10$^5$ CFU/ml in the well and the final concentrations of compound 3f ranged from 0.12 to 16 µg/ml. The plates were incubated at 37° C. for 3 weeks in 5% CO$_2$. The plates were read visually and the minimum concentration of the compound showing no turbidity was recorded as MIC.

Results: Compound 3f was active on sensitive, MDR and XDR clinical isolates of *M. tuberculosis*.

TABLE 2

Anti-tubercular activity of 3f against resistant *M. tuberculosis* strains.

| | MIC(µg/mL) | |
|---|---|---|
| | *M. tuberculosis* XDR-1 (XDR- strain) * | *M. tuberculosis* -617 (MDR- strain) * |
| Compound 3f | 0.5 | 0.5 |
| TLM | 25 | 25 |
| Isoniazid | 0.5 | 128 |

* Clinical isolates resistant to rifampicin and isoniazid

Example 27

Cytotoxicity Assay of Compound 3f

Cell Culture:

The study was carried out using AML-12 cells line (ATCC-USA). Cells were grown in Dulbecco's Modified Eagle's Medium (DMEM) containing 10% fetal calf serum (FCS) and supplemented with 100 units/ml penicillin, 100 µg/ml streptomycin, 0.005 mg/ml insulin, 0.005 mg/ml transferrin, 5 ng/ml selenium, and 40 ng/ml dexamethasone, in a humidified atmosphere in 5% $CO_2$ at 37° C., and were sub-cultured at 1:5 ratio once a week.

Cell Treatment:

Cells were plated at a density of $3 \times 10^4$ cells/cm$^2$ and maintained in culture medium for 12 h after trypsinization. Cells were seeded onto 96-well plates and FCS was reduced to 5% for the experiment. Stock solutions of compound 3f were prepared fresh to avoid oxidation. Cells were incubated with the compounds (2-100 µg/ml) for 24 hrs.

Cytotoxicity Assays:

After the completion of treatment, the medium was removed and cell viability was evaluated by assaying for the ability of functional mitochondria to catalyze the reduction of 3-(4,5-dimethylthiazol-2-yl)-2,5-diphenyltetrazolium bromide (MTT) to form formazan salt by mitochondrial dehydrogenases, and determined by Elisa reader at 565 nm (Multiskan Spectrum; Thermo Electron Corporation, USA). Percentage cytotoxicity was calculated with respect to the untreated cells.

Results:

Compound 3f was not toxic up to 100 µg/ml concentration. The safety index, which is the ratio of MIC to cytotoxicity was >433 µg/ml.

TABLE 3

Cytotoxicity assay on cell line AML-12(µg/mL)

| Compound code | Compound (µg/mL) | % cytotoxicity |
|---|---|---|
| 3f | 2 | 2.4 |
| | 5 | 9.0 |
| | 10 | 9.1 |
| | 25 | 8.5 |
| | 50 | 8.7 |
| | 100 | 14.9 |

NOTE:
$IC_{50}$ >433 µg/ml (extrapolate)

Example 28

In Vivo Efficacy of Compound 3f in Murine Model of *M. tuberculosis* H37Rv Infection In Vivo Assay:

The Compound 3f used in this study (>995 potency). The compound 3f was tested in vivo at 25 mg/kg. Rifampicin at 20 mg/kg was also tested as positive control. For in vivo studies compound and rifampicin was dissolved in pure DMSO and formulation was prepared 50% PEG in water for oral administration. The final concentration of DMSO was less than 0.1% v/v.

Animals:

The institutional animal Ethics committee of the Indian Institute of Integrative Medicine (CSIR, Jammu) approved all experimental protocols with animals and the use of animals. The animals were bred and maintained under standard husbandry conditions; viz. humidity, temperature (25±2° C.). 8-week-old female (BALB/c) mice 20-22 gm by weight were used for the efficacy studies. Animals were allowed 1 week of acclimation before intake into experimental studies. Feed and water were given ad libitum.

Infection of *M. tuberculosis*:

*M. tuberculosis* (H37Rv) for infection was grown by the culturing of bacteria from Lowenstein-Jensen slant in Middlebrooke 7H9 medium on a rotary shaker for 10 days at 37° C. Infections with *M. tuberculosis* were administered by the intranasal route with $5 \times 10^6$ CFU/ml in a 20 µl volume per mouse. The mice were sacrificed after week post infection (early control), and bacterial numbers in the lungs were determined by macerating the organs (lung) and plating serial tenfold serial dilution on Middlebrook 7H10 agar plates in triplicates. Treatment started one week post infection and groups were treated daily for 4 weeks with oral administration of rifampicin (20 mg/kg) and compound 3f (25 mg/kg).

Assessment of Bacterial Load:

Eight infected mice were sacrificed from the control group 7 day after the infection (before the initiation of treatment) to obtain the initial CFU load of *M. tuberculosis* H37Rv at the initiation of treatment. In the 3f treated groups, the mice sacrificed after 4 weeks of treatment. The lungs of the sacrificed mice were aseptically removed and homogenized in 1 ml of sterile normal saline containing 0.05% of Tween 80. Viable bacteria were quantitated by plating 10-fold serial dilutions in duplicates on Middlebrook, 7H10 agar supplemented with 10% OADC (oleic acid albumin dextrose catalase, Becton Dickinson, Sparks, Md.) and incubated at 37° C. in 5% $CO_2$ for 4-6 weeks. CFU per organ sample was counted and expressed as $log_{10}$ CFU per organ. CFU during in-vivo studies were determined on Middlebrook 7H10 plates supplement with 10% OADC containing Vancomycin 10 µg/ml, Amphoterecin 10 µg/ml, Nalidaxic acid 25 µg/ml. Drugs was added to minimize the chances of contamination during the incubation period. This drug concentration had no effect on *M. tuberculosis* growth. Rifampicin was also tested at 20/mg/kg body wt as positive control.

Results:

The compound 3f exhibited bacteriostatic activity as the log CFU in lungs was same as early control at the start of treatment.

TABLE 4

| | In vivo: | |
|---|---|---|
| Treatment group[a] | n[b] | Log₁₀ CFU/left Lung (mean ± SD) |
| Early Control | 8 | 6.0 ± 0.25 |
| Late Control | 7[c] | 7.1 ± 0.37 |
| RIF (20 mg/kg) | 7[c] | 2.0 ± 0.41 |
| 3f (25 mg/kg) | 6[d] | 6.2 ± 0.34 |

[a]Treatment was started 1 week after mice received ≈1 × 10⁶ viable mycobacteria intranasal. The drugs were evaluated at the following doses: RIF, 20 mg/kg; 3f 25 mg/kg for 4 weeks (PO x OD).
[b]Number of mice per group.
[c]One mouse found dead during therapy.
[d]Two mice found dead during therapy.

ADVANTAGES OF PRESENT INVENTION

Remarkable activity against MDR- and XDR-isolates of *M. tuberculosis*.

Combination of these compounds with first line anti-TB drugs will be aimed at shortening the treatment time of tuberculosis.

We claim:

1. A Quinolylpiperazino substituted thiolactone compound of the formula:

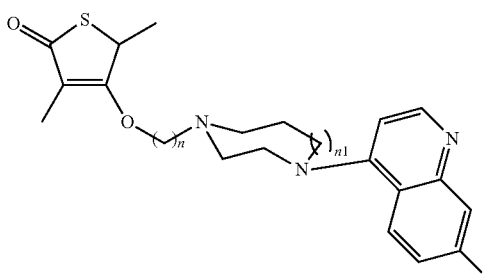

Formula A wherein, n=5-12, $n_1$=0, or 1, and R=$CF_3$, or Cl.

2. Quinolylpiperazino substituted thiolactone compounds according to claim 1, wherein the variables n, $n_1$ and R are quantified and the resultant compounds are categorized as 3a-f, 4a-f, 5a-f, 6a-f, such that:

3a-f, R = $CF_3$
4a-f, R = Cl 5a-f, R = $CF_3$
6a-f, R = Cl

| 3/4/5/6 | a | b | c | d | e | f |
|---|---|---|---|---|---|---|
| n | 5 | 6 | 8 | 9 | 10 | 12 |

3. Quinolylpiperazino substituted thiolactone compounds according to claim 1, wherein the variables n, n1 and R are quantified and the resultant compounds are categorized as 3a-f, 4a-f, 5a-f, 6a-f, such that the following compounds are created:
   3,5-dimethyl-4-[(5-4-[7-(trifluoromethyl)-4-quinolyl] piperazinopentyl)oxy]-5H-thiophen-2-one (3a);
   3,5-dimethyl-4-[(6-4-[7-(trifluoromethyl)-4-quinolyl] piperazinohexyl)oxy]-5H-thiophen-2-one (3b);
   3,5-dimethyl-4-[(8-4-[7-(trifluoromethyl)-4-quinolyl] piperazinooctyl)oxy]-5H-thiophen-2-one (3c);
   3,5-dimethyl-4-[(9-4-[7-(trifluoromethyl)-4-quinolyl] piperazinononyl)oxy]-5H-thiophen-2-one (3d);
   3,5-dimethyl-4-[(10-4-[7-(trifluoromethyl)-4-quinolyl] piperazinodecyl)oxy]-5H-thiophen-2-one (3e);
   3,5-dimethyl-4-[(12-4-[7-(trifluoromethyl)-4-quinolyl] piperazinododecyl)oxy]-5H-thiophen-2-one (3f);
   3,5-dimethyl-4-(5-[4-(7-chloro-4-quinolyl)piperazino] pentyloxy)-5H-thiophen-2-one (4a);
   3,5-dimethyl-4-(6-[4-(7-chloro-4-quinolyl)piperazino] hexyloxy)-5H-thiophen-2-one (4b);
   3,5-dimethyl-4-(8-[4-(7-chloro-4-quinolyl)piperazino] octyloxy)-5H-thiophen-2-one (4c);
   3,5-dimethyl-4-(9-[4-(7-chloro-4-quinolyl)piperazino] nonyloxy)-5H-thiophen-2-one (4d);
   3,5-dimethyl-4-(10-[4-(7-chloro-4-quinolyl)piperazino] decyloxy)-5H-thiophen-2-one (4e);
   3,5-dimethyl-4-(12-[4-(7-chloro-4-quinolyl)piperazino] dodecyloxy)-5H-thiophen-2-one (4f);
   3,5-dimethyl-4-[(5-4-[7-(trifluoromethyl)-4-quinolyl]-1, 4-diazepan-1-ylpentyl)oxy]-5H-thiophen-2-one (5a);
   3,5-dimethyl-4-[(6-4-[7-(trifluoromethyl)-4-quinolyl]-1, 4-diazepan-1-ylhexyl)oxy]-5H-thiophen-2-one (5b);

3,5-dimethyl-4-[(8-4-[7-(trifluoromethyl)-4-quinolyl]-1,4-diazepan-1-yloctyl)oxy]-5H-thiophen-2-one (5c);

3,5-dimethyl-4-[(9-4-[7-(trifluoromethyl)-4-quinolyl]-1,4-diazepan-1-ylnonyl)oxy]-5H-thiophen-2-one (5d);

3,5-dimethyl-4-[(10-4-[7-(trifluoromethyl)-4-quinolyl]-1,4-diazepan-1-yldecyl)oxy]-5H-thiophen-2-one (5e);

3,5-dimethyl-4-[(12-4-[7-(trifluoromethyl)-4-quinolyl]-1,4-diazepan-1-yldodecyl)oxy]-5H-thiophen-2-one (5f);

3,5-dimethyl-4-(5-[4-(7-chloro-4-quinolyl)-1,4-diazepan-1-yl]pentyloxy)-5H-thiophen-2-one (6a);

3,5-dimethyl-4-(6-[4-(7-chloro-4-quinolyl)-1,4-diazepan-1-yl]hexyloxy)-5H-thiophen-2-one (6b);

3,5-dimethyl-4-(8-[4-(7-chloro-4-quinolyl)-1,4-diazepan-1-yl]octyloxy)-5H-thiophen-2-one (6c);

3,5-dimethyl-4-(9-[4-(7-chloro-4-quinolyl)-1,4-diazepan-1-yl]nonyloxy)-5H-thiophen-2-one (6d);

3,5-dimethyl-4-(10-[4-(7-chloro-4-quinolyl)-1,4-diazepan-1-yl]decyloxy)-5-H-thiophen-2-one (6e);

3,5-dimethyl-4-(12-[4-(7-chloro-4-quinolyl)-1,4-diazepan-1-yl]dodecyloxy)-5H-thiophen-2-one (6f).

4. A method of treating *M. tuberculosis* H37Rv using a Quinolylpiperazino substituted thiolactone compound of the formula:

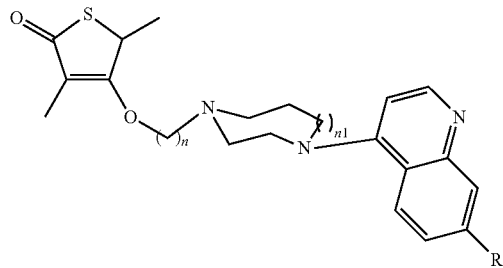

wherein n=5-12, $n_1$=0, or 1, and R=$CF_3$, or Cl.

5. The method of claim 4, wherein the variables n, n1 and R are quantified and the resultant compounds are categorized as 3a-f, 4a-f, 5a-f, 6a-f, such that:

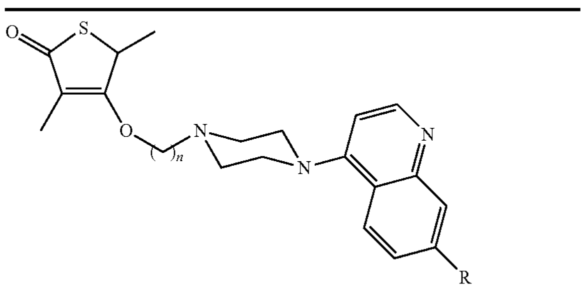

3a-f, R = $CF_3$
4a-f, R = Cl

-continued 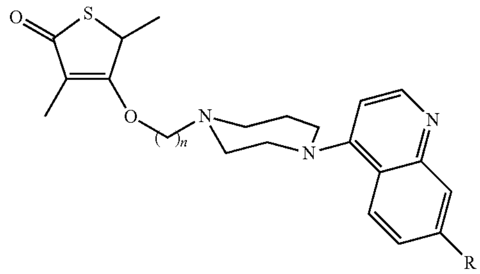 5a-f, R = $CF_3$
6a-f, R = Cl

| 3/4/5/6 | a | b | c | d | e | f |
|---|---|---|---|---|---|---|
| n | 5 | 6 | 8 | 9 | 10 | 12. |

6. The method of claim 4, wherein minimum inhibitory concentration (MIC) used for in vitro activity against *M. tuberculosis* H37Rv is in the range of 0.5-16 µg/ml respectively at an exposure period of at least 3 weeks.

7. The method of claim 5, wherein the compound 3f exhibits in vitro activity against *M. tuberculosis* MDR-strains, *M. tuberculosis* XDR-strains and *Mycobacterium tuberculosis* H37Rv, Cl.

8. The method of claim 5, wherein compound 3f was not toxic on cell line AML-12 up to 100 µg/ml concentration.

9. A process for the preparation of a Quinolylpiperazino substituted thiolactone compound of the formula:

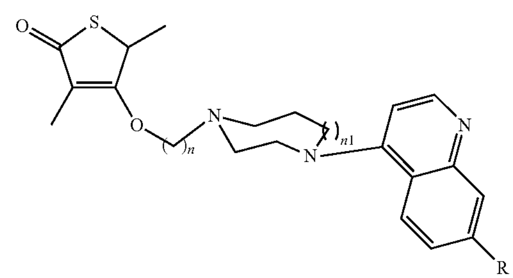

wherein, n=5-12, $n_1$=0 or 1, and R=$CF_3$ or Cl, said process comprising the steps of:

a) adding a base, dibromoalkane, in the solution of 4-hydroxythiolactone in dry acetone in the molar ratio ranging between 4:2.5:1 to 4:4:1;
b) refluxing the reaction mixture as obtained in step (a) at temperature ranging between 55-60° C. for a period ranging between 36-48 h;
c) filtering the reaction mixture as obtained in step (b) followed by evaporating the solvent in vacuo to obtain crude product;
d) purifying the crude product as obtained in step (c) by column chromatography to obtain pure bromoalkyl derivative of thiolactone;
e) adding bromoalkyl derivative of thiolactone as obtained in step (d), substituted 4-quinopipefazine/homopiperazine and a base in dry acetone followed by refluxing at temperature ranging between 55-60° C. for a period ranging between 36-48 h;
f) filtering the reaction mixture as obtained in step (e) to obtain crude product;

g) purifying the crude product as obtained in step (f) by column chromatography using ethyl acetate:hexane (7:3) as eluent to obtain pure quinolylpiperazino substituted thiolactone compounds.

10. A process as claimed in claim 9, wherein dibromoalkane used in step (a) is selected from the group consisting of 1,5-dibromopentane, 1,6-dibromohexane, 1,8-dibromooctane, 1,9-dibromononane, 1,10-dibromodecane and 1,12-dibromododecane.

11. A process as claimed in claim 9, wherein substituted -4-quinopiperazine/homopiperazine used in step (e) is selected from the group consisting of 7-trifluoromethyl-4-quinolylpiperazine, 7-chloro-4-quinolylpiperazine, 7-trifluoromethyl-4-quinolylhomopiperazine and chloro-4-quinolylhomopiperazine.

12. A process as claimed in claim 9, wherein base used in step (a) and (e) is selected from the group consisting of $K_2CO_3$ and triethylamine.

13. A process as claimed in claim 9, wherein yield of quinolylpiperazino substituted thiolactone compounds is in the range of 70-90%.

* * * * *